US00PP26872P2

(12) United States Plant Patent
Koplin

(10) Patent No.: US PP26,872 P2
(45) Date of Patent: Jun. 28, 2016

(54) RASPBERRY PLANT NAMED 'KOPLINBERRY'

(50) Latin Name: *Rubus idaeus*
Varietal Denomination: Koplinberry

(71) Applicant: Kal Evan Koplin, Sandy Springs, GA (US)

(72) Inventor: Kal Evan Koplin, Sandy Springs, GA (US)

(73) Assignee: It Saul Plants LLC, Alpharetta, GA (US)

( * ) Notice: Subject to any disclaimer, the term of this patent is extended or adjusted under 35 U.S.C. 154(b) by 128 days.

(21) Appl. No.: 14/120,126

(22) Filed: Apr. 28, 2014

(51) Int. Cl.
*A01H 5/08* (2006.01)

(52) U.S. Cl.
USPC ..... Plt./204

(58) Field of Classification Search
USPC ..... Plt./204
See application file for complete search history.

*Primary Examiner* — June Hwu
(74) *Attorney, Agent, or Firm* — Penny J. Aguirre

(57) ABSTRACT

A new cultivar of *Rubus idaeus*, 'Koplinberry', characterized by its trailing plant habit with arching canes that require trellising, its ever-blooming plant habit with floricanes flowering from March to hard frost and primocanes flowering in summer in Atlanta, Ga., its rapidly maturing canes that yield edible fruit in the first season of growth, its long harvest season with non-uniform fruit ripening; lasting from April to November in northern Georgia, its fruit that are borne beneath the foliage, and its leaves that have, primarily, three leaflets and are medium green in color, and its canes that are colored medium green in the shade, red in full sun, and brown near the base.

2 Drawing Sheets

Botanical classification: *Rubus idaeus.*
Cultivar designation: 'Koplinberry'.

BACKGROUND OF THE INVENTION

The present invention relates to a new and distinct cultivar of raspberry plant, botanically known as *Rubus idaeus* 'Koplinberry' and will be referred to hereinafter by its cultivar name, 'Koplinberry'. 'Koplinberry' is grown for fruit production and is particularly well suited for homeowners and garden market use in Georgia.

'Koplinberry' was discovered by one of the Inventors as a chance seedling in a garden in Atlanta, Ga., in 2007. 'Koplinberry' resulted from the open pollination of raspberry plants of unknown varieties that were growing in the Inventor's garden and the parentage is therefore unknown.

Asexual propagation of the new cultivar was first accomplished by one of the Inventors by division of rooted canes in Atlanta, Ga. in summer of 2010. Asexual propagation of the new cultivar by division of rooted canes and in vitro propagation initiated by meristem tissue has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Koplinberry' as a new and unique cultivar of *Rubus.*

1. 'Koplinberry' exhibits a trailing plant habit with arching canes that require trellising.
2. 'Koplinberry' exhibits an ever-blooming plant habit with floricanes flowering from March to hard frost and primocanes flowering in summer in Atlanta, Ga.

3. 'Koplinberry' exhibits rapidly maturing canes that yield edible fruit in the first season of growth.
4. 'Koplinberry' exhibits a long harvest season, with non-uniform fruit ripening, lasting from April to November in Northern Georgia.
5. 'Koplinberry' exhibits fruit that are borne beneath the foliage.
6. 'Koplinberry' exhibits leaves that have primarily three leaflets
7. 'Koplinberry' exhibits canes that are colored medium green in the shade, red in full sun, and brown near the base.

'Koplinberry' can be most closely compared to the limited number of raspberry cultivars recommended to Georgia gardeners; 'Autumn Bliss' (U.S. Plant Pat. No. 6,597), 'Dormanred' (not patented), 'Polka' (not patented), 'Heritage' (not patented), and 'Redwing' (not patented). 'Koplinberry' can also be compared to the raspberry cultivar 'Prelude' (U.S. Plant Pat. No. 11,747). 'Autumn Bliss' differs from 'Koplinberry' in having erect canes and in having short fruiting laterals. 'Dormanred' is similar to 'Koplinberry' in having a trailing plant habit. 'Dormanred' differs from 'Koplinberry' in having rounder foliage, in having flowers that are pink in color, and in having fruit that is larger in size. 'Polka' differs from 'Koplinberry' in having a very upright plant habit and in having berries that are much more elongated in shape. 'Heritage' differs from 'Koplinberry' in having an upright plant habit and in being a late season primocane producer. 'Redwing' differs from 'Koplinberry' in having leaves primarily with five leaflets. 'Prelude' is similar to 'Koplinberry' in having an early fruiting season, in producing a fall primocane crop, and in having fruit with a similar shape, numbers of drupets, and average fruit weight. 'Prelude' differs from 'Koplinberry' in having sparse spine density, in having canes that are self-supporting, in having fruits that separate from the receptacle with a smooth collar (rather than indented), and in having fruit that is openly positioned (rather than under the foliage).

BRIEF DESCRIPTION OF THE DRAWINGS

The accompanying colored photographs illustrate the overall appearance and distinct characteristics of the new *Rubus*. The photographs in FIG. 1 and FIG. 2 were taken of five year-old plants as grown in the ground in Atlanta, Ga. The photograph in FIG. 3 was taken of ten-month old plants as grown from tissue culture in seven-gallon containers in Atlanta, Ga.

The photograph in FIG. 1 provides a close-up view of a fruiting branch of 'Koplinberry' showing berries at different stages of maturation.

Figure 1:
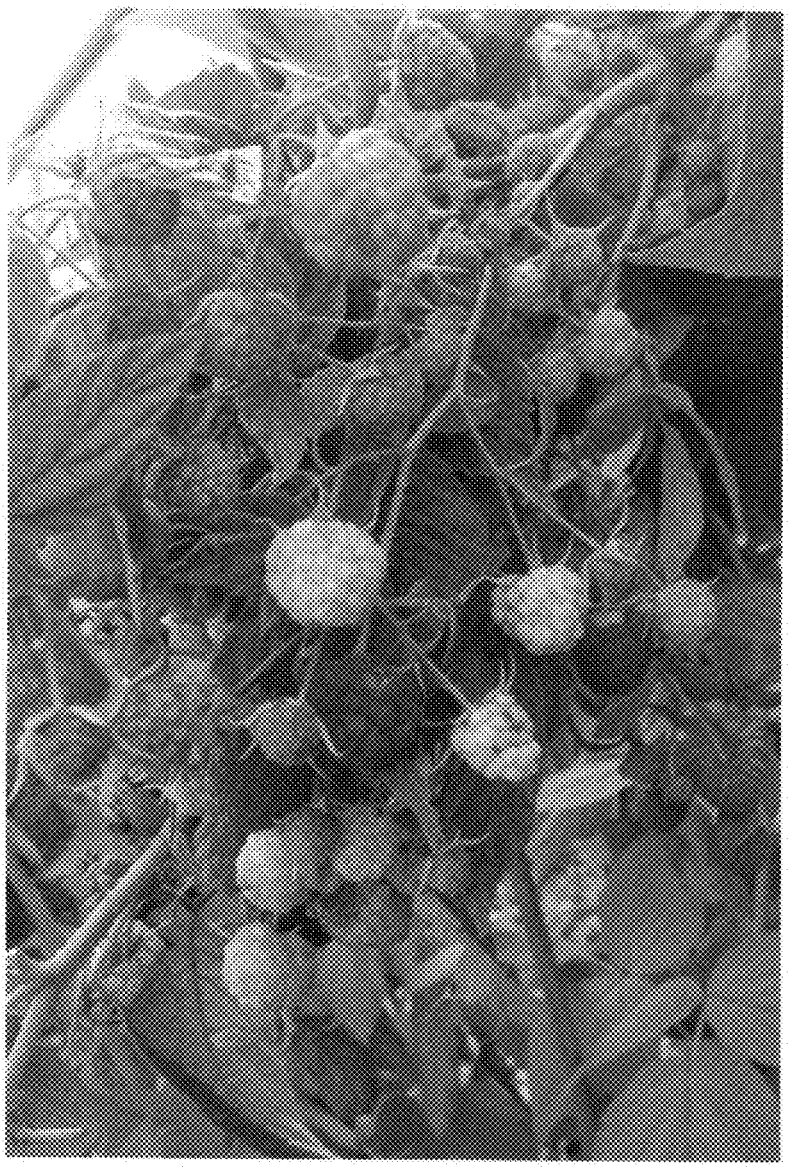
Figure 2:
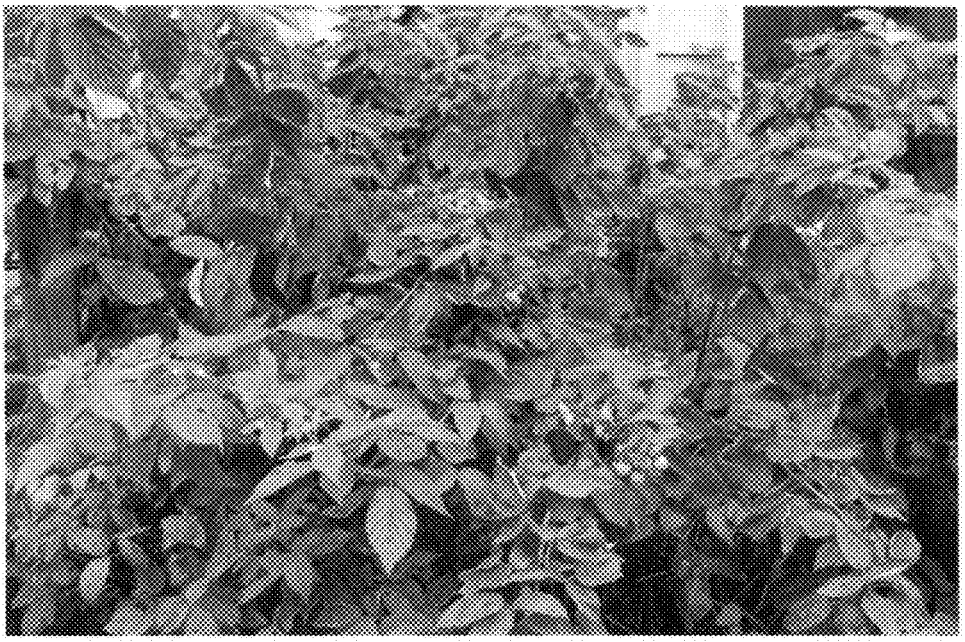

The photograph in FIG. 2 provides a view of the overall plant habit of 'Koplinberry'.

Figure 3:
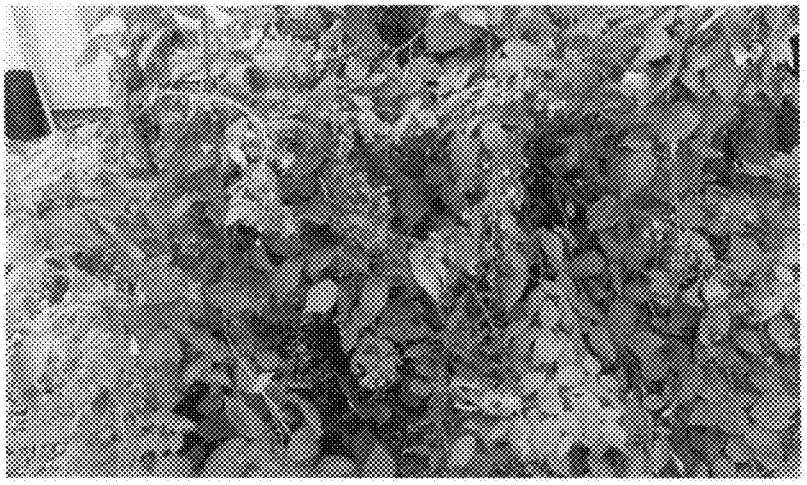

The photograph in FIG. 3 provides a view of potted plants, bearing fruit in the first year of growth, of 'Koplinberry'.

The colors in the photographs are as close as possible with the photographic and printing technology utilized. The colors in the photograph may differ slightly from the color values cited in the detailed botanical description, which accurately describe the colors of the new *Rubus*.

DETAILED BOTANICAL DESCRIPTION OF THE PLANT

The following is a detailed description of five year-old plants of the new cultivar as grown outdoors in the ground in Atlanta, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Ever-blooming plant habit with floricanes flowering from March to hard frost and primocanes flowering from June until frost in Atlanta, Ga.

*Plant habit.*—Perennial, trailing shrub with arching canes, needs trellising.

*Height and spread.*—Reaches an average of 1.4 to 1.8 m (5 to 6 ft) in height with arching canes and 1.8 m in width.

*Hardiness.*—Unknown, grown for southern climates.

*Environmental conditions.*—Tolerant to heat and humidity.

*Diseases and pests.*—No susceptibility or resistance to diseases or pests has been observed.

*Root description.*—Fibrous and fine.

*Branching habit.*—Basal branching with lateral branches produced if cut back.

*Propagation.*—Tissue culture (preferred) or cane division.

*Growth rate.*—Vigorous.

Cane description:

*Cane size.*—Primocanes; an average of 1.4 m in length and 4.5 mm in width, floricanes; an average of 1.6 m in length and 5 mm in width at mid cane (ranges from 1 cm at base to 3 mm at apex).

*Cane color.*—Primocanes; 145A and becoming suffused with 183B to 183D as it matures on sun exposed surface, floricanes; shaded surface a blend between 144B and 145A, sun exposed surface; a blend of 183B and 200A near the base.

*Cane surface.*—Primocanes; glabrous with sparse prickles, floricanes; glabrous and densely covered with prickles.

*Prickles.*—(Both primocanes and floricanes); an average of 1.7 mm in length and 0.5 mm in width, average distance between prickles 3 mm, color; the same as the cane position where they are located.

*Stipules.*—(Both primocanes and floricanes); 1 to 2 per petiole, very fine, an average of 5 mm in length, lanceolate in shape, 144C in color.

*Primocane emergence.*—Medium.

*Vegetative bud burst.*—Early.

Foliage description:

*Leaf shape.*—Ovate in overall form.

*Leaf division.*—3 leaflets (occasionally 5).

*Leaf attachment.*—Petiolate.

*Leaf orientation.*—Outward to pendant, position is free.

*Leaf size.*—An average of 18 cm in length and 15 cm in width.

*Leaf quantity.*—An average of 21 per cane 1 m in length.

*Internode length.*—An average of 3 cm.

*Leaflet shape.*—Ovate.

*Leaflet base.*—Rounded to cuneate.

*Leaflet apex.*—Acute to acuminate.

*Leaflet venation.*—Pinnate, color on upper surface new growth; N144A and mature leaflets; a blend of N137B and 141C, color on lower surface on new and mature leaflets; 144D.

*Leaflet margins.*—Serrate and occasionally separated into 3 lobes oblanceolate in shape.

*Leaflet arrangement.*—One terminal and 2 as lateral pairs.

*Leaflet attachment.*—Sessile.

*Leaflet surface.*—Upper surface glabrous and rugose between veins especially when newly opened, lower surface finely puberulent.

*Leaflet color.*—New growth; upper surface a blend of N144A and 187A, lower surface 192D, mature growth; upper surface a blend of N137B and 141C, lightly suffused with 187A, lower surface 191D.

*Leaflet size.*—An average of 12 cm in length and 5.5 cm in width.

*Leaflet substance.*—Thin.

*Petioles.*—Round in shape, an average of 4 cm in length and 2 mm in width with expanded region at attachment 5 mm in width and 6 mm in length, color; sun exposed surface 144B to 144D, upper surface suffused with 173A with expanded region 144A and shaded surface 144A to 144B with expanded region 143A, all surfaces pubescent and sparsely covered with small prickles 1 mm in length and 166A in color.

*Rachis.*—Round in shape, an average of 2 cm in length and 1 mm in width, color; sun exposed surface 144B to 144D, upper surface suffused with 173A and shaded surface 144A to 144B, all surfaces pubescent and sparsely covered with small prickles 1 mm in length and 166A in color.

Inflorescence description:

*Inflorescence.*—Cyme, an average of 10 cm in length (from base of rachis) and 1.5 cm in width.

*Lastingness of inflorescence.*—About 4 days.

*Peduncle.*—Oval in shape, an average of 6 cm in length and up to 1.5 mm in width, internode length between flowers an average of 8 mm, 144A to 144B in color, glabrous surface and moderately covered with prickles N77A in color, an average of 1 mm in length and 0.5 mm in width, average distance between prickles 2 mm.

*Pedicels.*—Oval in shape, an average of 3 cm in length and 1 mm in width, 144A to 144BB in color, surface is glabrous and moderately covered with prickles N77A in color, an average of 1 mm in length and 0.5 mm in width, average distance between prickles 2 mm.

*Flower buds.*—Triangular in shape with a wide flat bottom and apex narrowing to a point, up to 8 mm in width and 10.5 mm in length, 144A in color, surface is pubescent and covered with prickles on basal part an average of 1 mm in length and 0.5 mm in width 187A to 187B in color, seams of sepals 155A in color.

*Flower type.*—Spreading calyx with a center of a ring of numerous upright stamens and with numerous pistils in the center, petals are quickly shed upon opening.

*Flower number.*—An average of 6 per cyme.

*Flower size.*—Average of 8 mm in depth and 2.5 cm in diameter.

*Sepals.*—Five, lanceolate-ovate in shape, held upright to horizontal, an average of 5 min in width and 13 mm in length, fused at base, acuminate apex, margins entire, color lower surface; 144B with margins 155A, color upper surface; 144A with margins 155A, pubescent upper and lower surface pubescent.

*Petals.*—Five, dropped just after flower opening, an average of 5 mm in length and 2 mm in width, obovate in shape, rounded apex, cuneate base, glabrous on upper and lower surfaces, thin, 155A in color.

*Androecium.*—An average of 100 stamens that form a concentric ring about 9 mm in diameter, inserted base of sepals, about 4 mm in length, filaments are NN155B in color, anthers dorsifixed, <1 mm in length, and 165A in color, pollen is not observed.

*Gynoecium.*—An average of 50 pistils, styles are an average of 4 mm in length and 155A in color, stigmas are very small and about 162C in color, ovaries are attached to receptacle at base, about 3.5 mm in length and 4 mm in width, ovate in shape, and N144D in color with strongly pubescent surface with hairs 155A in color.

Fruit description:

*Fruit number.*—An average of 120 per cane (average of 12 per node).

*Fruit presence on cane.*—Fruit is produced on 25% of the cane length (average of 43 cm).

*Fruit size.*—Aggregate an average of 2.05 cm in width and 1.8 cm in length.

*Fruit shape.*—Aggregate fruit is globose with flattened base.

*Druplets.*—An average of 85 per aggregate fruit, globose to oval in shape, an average of 4 mm in diameter and height, color when first formed; 145C, color when maturing; 160C changing to a blend between 27A to 27C and 38A to 38D, color when mature; 46A, color darkens slightly postharvest to about 59A, surface is glossy, style and stigma; persistent at maturity and extends from druplet an average of 1.5 mm, very fine, about 165A in color.

*Fruit lateral attitude.*—Drooping.

*Persistence of sepals.*—Persistent.

*Receptacle.*—Rounded-conical in shape, an average of 8 mm in diameter and 1 cm in depth, 157A in color.

*Fruit maturity in the garden.*—April to November in Atlanta, Ga.; fruit is produced over a long period due to variable ripening rate (continually ripening) and production on both floricanes and primocanes.

*Fruit production on young plants.*—Tissue culture plugs planted in April in 3-gallon containers will produce fruit the first year of growth from late summer until frost.

*Seed.*—Oval in shape, 1 per druplet, 2 mm in length, 1 mm in width, 164B in color.

*Flavor.*—Sweet raspberry.

*Fruit weight.*—An average of 3 grams per berry.

*Fruit attachment to the plug.*—Medium.

*Fruit firmness.*—Medium soft.

It is claimed:

1. A new and distinct cultivar of *Rubus* plant named 'Koplinberry' as herein illustrated and described.

* * * * *